United States Patent
Dolan et al.

(10) Patent No.: US 6,433,694 B1
(45) Date of Patent: Aug. 13, 2002

(54) SENSOR HAVING IMPROVED DESORPTION TIMES AND RELATED CONTROL CIRCUITRY

(75) Inventors: James P. Dolan; Patrick M. Dolan, both of Seattle, WA (US)

(73) Assignee: Adsistor Technology Inc., Seattle, WA (US)

(*) Notice: Subject to any disclaimer, the term of this patent is extended or adjusted under 35 U.S.C. 154(b) by 0 days.

(21) Appl. No.: 09/273,953

(22) Filed: Mar. 22, 1999

Related U.S. Application Data

(60) Provisional application No. 60/079,580, filed on Mar. 26, 1998.

(51) Int. Cl.$^7$ .............................................. G08B 21/00
(52) U.S. Cl. .................. 340/603; 340/632; 73/31.02; 73/31.05; 73/40.5 B; 73/46; 204/400; 324/691
(58) Field of Search ................................. 340/603, 604, 340/605, 521, 612, 632; 73/304, 40, 40.5 R, 46, 31.02, 31.06, 31.05; 338/34; 422/90, 98; 307/650; 324/691; 204/412, 431, 400

(56) References Cited

U.S. PATENT DOCUMENTS

| | | | | |
|---|---|---|---|---|
| 4,224,595 A | * | 9/1980 | Dolan ........................ | 340/521 |
| 4,752,761 A | * | 6/1988 | Dolan et al. ................ | 340/517 |
| 4,827,246 A | * | 5/1989 | Dolan et al. ................ | 340/521 |
| 5,341,128 A | * | 8/1994 | Keyser et al. ............... | 340/605 |
| 5,387,462 A | * | 2/1995 | Debe .......................... | 428/245 |
| 5,574,377 A | * | 11/1996 | Marquez-Lucero et al. | 324/533 |
| 5,589,630 A | * | 12/1996 | Wiegand et al. ........... | 73/23.42 |
| 5,594,162 A | * | 1/1997 | Dolan et al. ................ | 73/46 |

* cited by examiner

*Primary Examiner*—Edward Lefkowitz
*Assistant Examiner*—Davetta W. Goins
(74) *Attorney, Agent, or Firm*—Graybeal Jackson Haley LLP

(57) ABSTRACT

A sensor and method for rapidly determining the absence of a vapor in a gas or fluid is described as well as a method for constructing the sensor. The sensor comprises a resistive element having first and second leads; an elastomeric material in thermal contact with and surrounding a portion of the resistive element; and a stratum of electrically conductive particles surrounding a portion of the elastomeric material and electrically coupled to the first lead and a third lead. The method for determining the absence of a vapor comprises linking the sensor to a control means for preventing excessive adsorption; exposing the sensor to an environment; and monitoring the sensor. The method for constructing the sensor comprises applying an elastomeric material to the resistive element; applying a stratum of electrically conductive particles to the elastomeric material; electrically coupling one portion of the stratum to a first lead of the resistive element; and electrically coupling another portion of the stratum to a third lead. By adsorbing some of the vapor's molecules when the stratum of electrically conductive particles is exposed to a gas or fluid containing certain vapors, the stratum's electrical resistance changes. These changes are monitored by a control circuit that runs current through the resistive element when a threshold of adsorption has occurred. The heat from the resistor raises the temperature of the stratum and enables the stratum to shed the previously adsorbed vapor molecules.

18 Claims, 5 Drawing Sheets

SENSOR HAVING IMPROVED DESORPTION TIMES AND RELATED CONTROL CIRCUITRY

This application is a continuation of a provisional application No. 60/079,580 filed on Mar. 26, 1998.

FIELD OF THE INVENTION

The present invention generally pertains to chemical vapor sensors and related control circuitry, and more particularly to chemical vapor sensors having rapid desorption rates so as to provide rapid information concerning the decrease of chemical vapors in an environment.

BACKGROUND OF THE INVENTION

Adsorption-type sensors sensitive to hydrocarbon containing vapors have been used in various applications for many years. Common applications include the use of such sensors in marine (bilge and engine rooms), underground (wells and storage tanks), and similar applications. The purpose of these sensors is to provide information concerning the presence of hydrocarbon containing vapors to a monitoring system. To this end, these sensors were optimized to quickly detect chemical containing vapors, and especially hydrocarbon containing vapors, through adsorption since ambient conditions were presumptively without the presence of such compound containing vapors.

Examples of these sensors can be found in, for example, U.S. Pat. Nos. 3,045,198, 4,224,595, and 4,752,761, which are incorporated herein by reference. These sensors utilized electrically conductive adsorbent particles that were resiliently attached to a surface so that an electrically conductive path was formed through the particles. When subjected to a vapor containing hydrocarbons, for example, the resistance between the electrodes contacting the conductive adsorbent particles was increased. Improvements to the sensitivity and range of the sensor were achieved by using heterogeneous particles in a given conductive pathway, and providing control circuitry for carefully regulating the temperature of the particles.

As noted above, however, sensors of the type described were optimized to detect hydrocarbon containing vapors in ambient conditions generally lacking such adsorbates. Where the ambient conditions have a high concentration of hydrocarbon containing vapors, or liquid phase hydrocarbon containing compounds, the aforementioned optimizations generally fail. This shortcoming is important in view of the following.

Federal and local government agencies now require that gasoline dispensers be capable of recovering the gasoline vapor that is displaced from an automobile's tank by liquid gasoline during a refueling operation. This is usually accomplished by means of a vacuum vapor recovery system that works in conjunction with the fuel pumping system. A dual conduit hose and a compound nozzle are used to deliver liquid gasoline to a vehicle's tank while simultaneously drawing off the displaced gasoline vapors through a separate vacuum port near the tip of the nozzle. The vacuum system returns the displaced vapor back to the service station's underground storage tank as is best shown in FIG. 1. In such a manner, a system efficiency of approximately 95% can be achieved (Transfer emissions of 0.34 pounds of hydrocarbons per 1000 gallons dispensed; Fugitive emissions of 0.08 pounds of hydrocarbons per 1000 gallons dispensed).

The Environmental Protection Agency (EPA) has recently mandated that beginning in 1998, certain modifications must be made to new vehicle fuel systems to prohibit the displacement of fuel vapors resulting from filling actions to the environment. In essence, these on-board refueling vapor recovery systems (ORVRS) will take the place of a station equipped system, thereby obviating the need for any vacuum recovery system. However, if an ORVRS equipped vehicle is refilled from a vacuum recovery system equipped station, the system will only recover ambient air. While this may initially appear to be of no consequence, industry testing has shown that unacceptable quantities of gasoline vapor escape from the underground tank vents when ambient air is introduced into the vacuum vapor recovery system. As shown in FIG. 2, transfer emissions remain similar to those generated with the vacuum recovery system, however because of in increase in static pressure in the station storage tank, fugitive emissions are-increased by over 30 times. The result is a system efficiency of only 60% as opposed to 95%.

To provide a solution for selectively capturing only gasoline vapor containing air and not unnecessarily introduce ambient air into a station's fuel storage tanks, it would be most desirable to sense whether a refueling vehicle possessed an ORVRS so that a vacuum recovery system could be temporarily disabled so as to prevent this undesirable introduction of ambient air into the storage tank. Because there appears to be no standard physical configuration relating to the refueling nozzle, such sensing would likely be limited to determining the quality of the evacuated air, i.e., whether it contained a high vapor level of hydrocarbons which are found in all present fuels.

Since only vehicles manufactured and sold from 1998 and forward would be equipped with an ORVRS, the sensing means would have to be able to tolerate frequent exposure to air that was highly saturated with hydrocarbon compounds including solvents such as gasoline or diesel fuel. The sensing means would have to not deteriorate over prolonged exposure to such an environment. Moreover, the sensing means would have to have a rapid response time so that an effective interruption of a vacuum recovery system could be carried out prior to a significant introduction of ambient air into the storage tank. Gasoline dispenser manufacturers estimate that the detection of ambient air in the vacuum recovery system must occur within 10 seconds of its introduction into the vacuum port on the nozzle.

The sensors of the prior art fail to meet these needs since they are optimized to operate in ambient air conditions with only an occasional exposure to destructive hydrocarbon containing vapors. Their response time, as determined by a desorption time factor, fails to indicate the presence of ambient air after exposure to hydrocarbon containing vapor within the recommended 10 seconds. In addition, their longevity when placed in the harsh environment of solvent vapors is questionable at best.

SUMMARY OF THE INVENTION

The present invention is drawn to improvements in hydrocarbon adsorption sensors and related circuitry. The improvements relate to the manner of intended use of the sensor, namely use in an environment wherein the presence of the compound being sensed is normal and rapid sensing of conditions lacking the compound is desired. To this end, the sensor of the present invention in a first embodiment comprises an electrically resistive element having a first conductive lead and a second conductive lead; an elastomeric material in thermal contact with the resistive element; a stratum of conductive particles generally adhered to and at least partially covering the elastomeric material to form a sensitive surface having variable electrical resistance properties wherein a first portion of the conductive layer is electrically coupled with the first conductive lead; and a third conductive lead is electrically coupled with a second portion of the conductive stratum physically apart from the first portion.

Features of the sensor that improve its rapid determination of hydrocarbon absence include using 50 micron or smaller conductive particles, using 100% silicone with no adjuncts as the elastomeric material, using the resistive element as a heat source to periodically desorb the adsorbed compounds from the stratum, and utilizing a simple control circuitry to control the resistive element heating cycle. In addition to sensitivity improvements, another feature is directed to improving the longevity of the sensor. This feature is accomplished by tapering at least one portion of the elastomeric material adjacent a resistive element lead so that when an end cap is placed thereat to achieve electrical conduction there between, neither the cap nor the stratum will be undesirably stressed when the elastomeric material expands due to exposure to solvents or the like.

The control circuit for use with the sensor broadly described above is intended to sense the level of stratum resistance and cause desorption therefrom when the sensor reaches a threshold adsorption level. This function is carried out by a negative feedback circuit and comprises a first voltage divider and a second voltage divider operatively coupled to a voltage comparator; and a power amplifier operatively coupled to an output of the voltage comparator and to an electrically resistive element of a sensor having a variable resistance sensitive surface, wherein the sensitive surface comprises a part of the first voltage divider. By this arrangement, power is selectively applied to the power amplifier by the comparator for distribution to the resistive element when a predetermined condition exists between the first and the second voltage dividers. Because a portion of the first voltage divider comprises the sensitive surface, the resistance of the sensitive surface is compared to a reference resistance that is part of the second voltage divider. When the sensitive surface resistance increases beyond a threshold due to excessive adsorption, the comparator causes power to be applied to the resistive element of the sensitive surface to heat the same, and cause partial desorption of the sensitive surface, thereby restoring its ability to rapidly desorb when exposure to fresh air occurs.

DESCRIPTION OF THE PREFERRED EMBODIMENTS

The present invention is intended to be used in an environment at least frequently, if not substantially, exposed to volatile, organic solvents such as gasoline. The purpose of the invention is to detect the absence of these solvents in a gaseous environment. Therefore, the objective is to construct the invention in such a manner so as to optimize the recovery period from exposure to such gasses to non-exposure so that monitoring equipment may be provided with reliable information concerning the relative absence of vapors containing organic solvents.

Because the invention operates using the principles of Van der Waal's adsorption forces of compounds to vary the resistance of the sensor, the following features are intended to optimize the desorption rate of the sensor. While each feature improves the desorption rate, a preferred embodiment utilizes most if not all features to achieve maximum performance.

Figure 1:
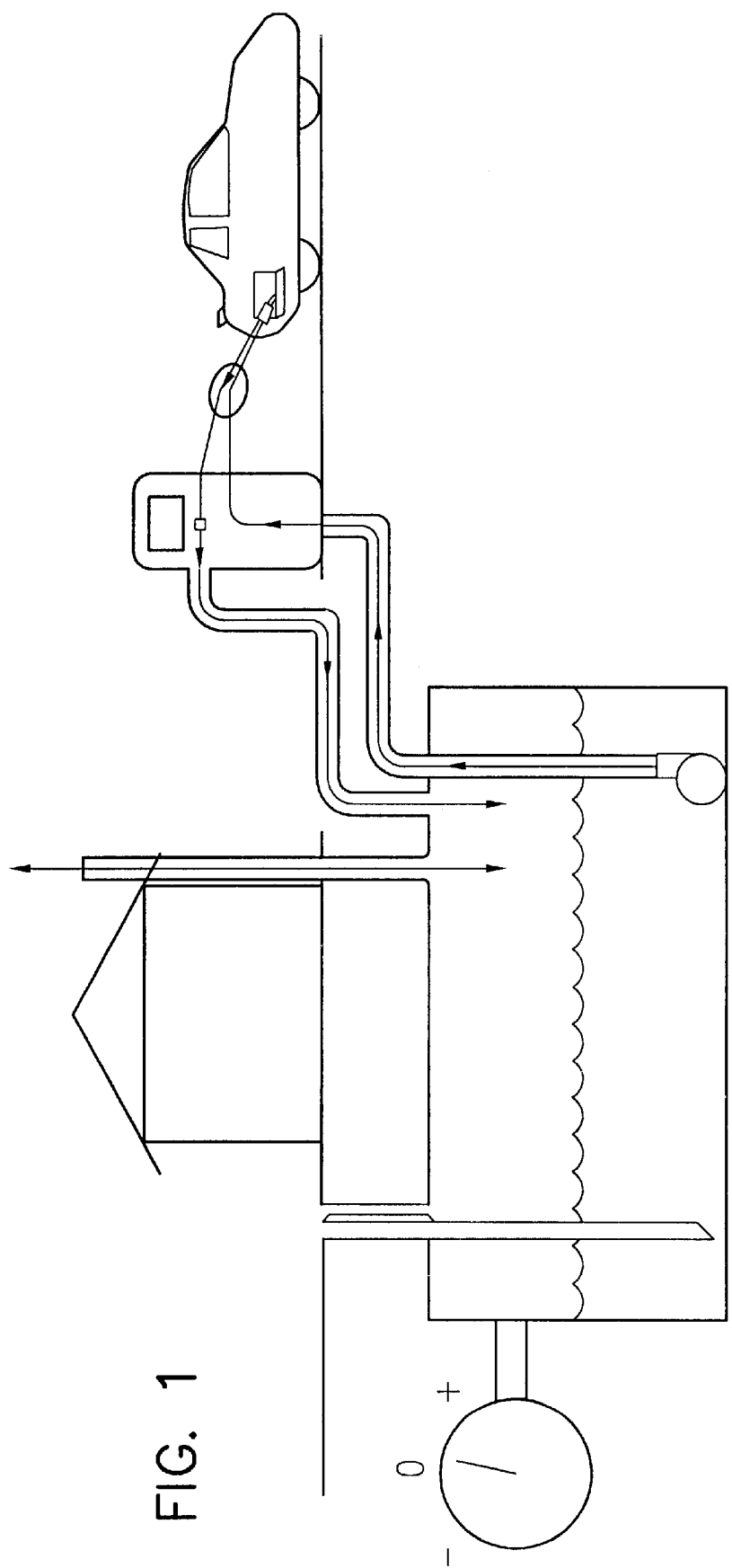
FIG. 1 is a schematic diagram of refueling station employing a vacuum vapor recovery system being used on a non-modified vehicle.
Figure 2:
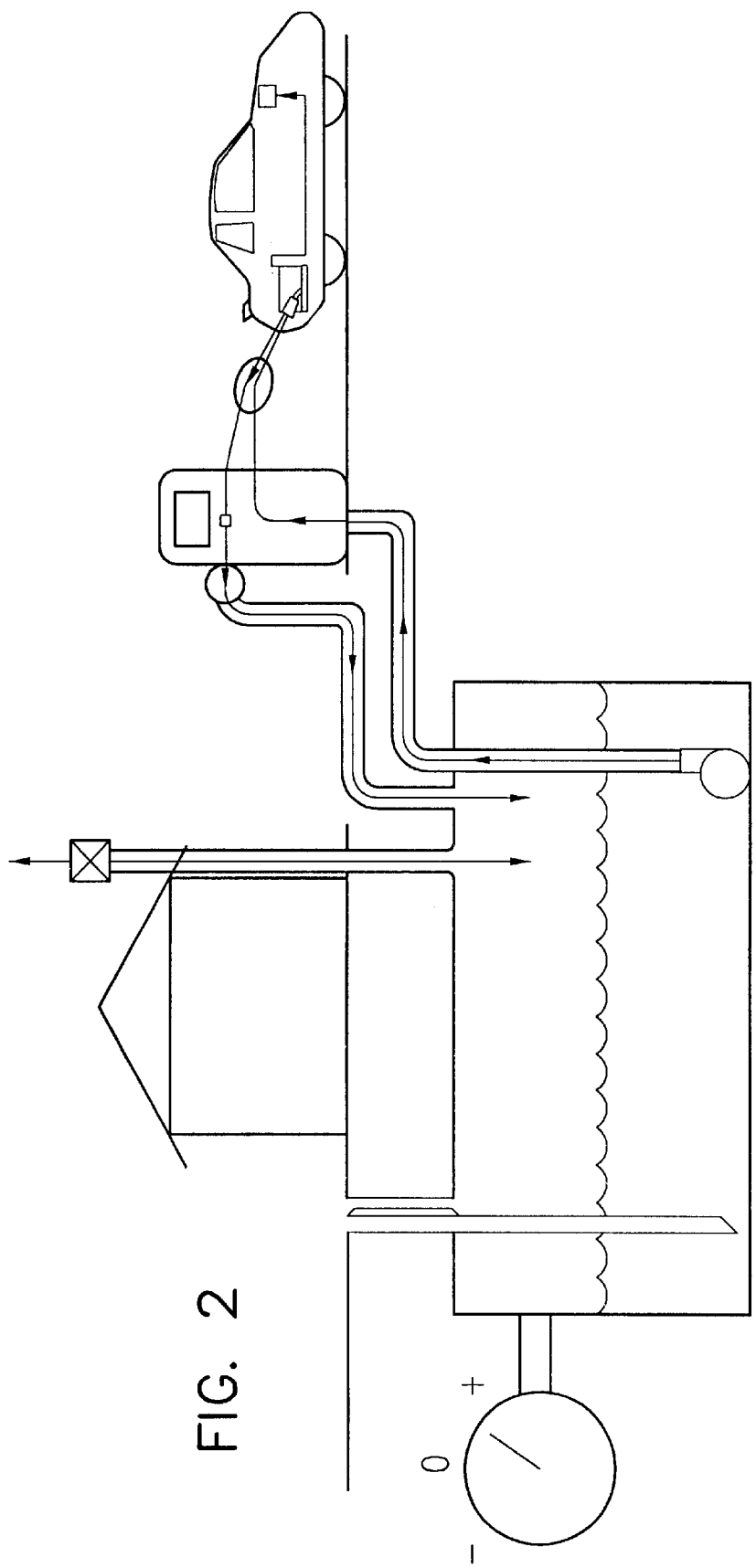
FIG. 2 is a schematic diagram similar to FIG. 1 but that the vehicle has been modified to include an onboard refueling vapor recovery system and a vent check valve has been installed.
Figure 3:
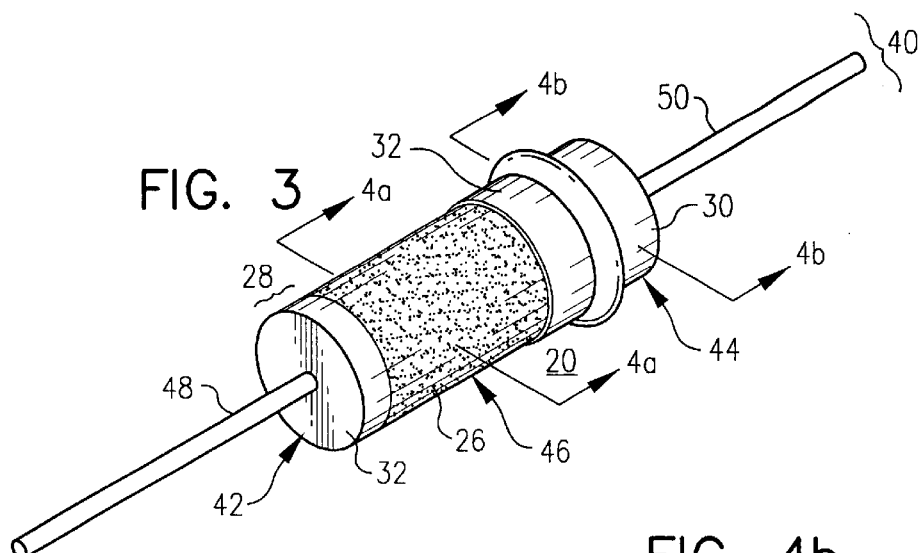
FIG. 3 is a perspective view of the sensor of the present invention.
Figure 4A:
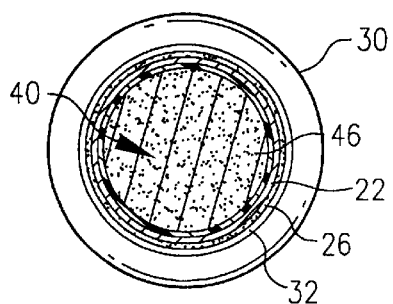
FIG. 4a is a cross section of the sensor taken substantially along the line 4a—4a in FIG. 3.
Figure 4B:
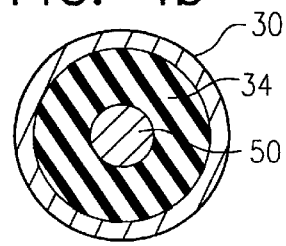
FIG. 4b is a cross section of the sensor taken substantially along the line 4b—4b in FIG. 3.

Turning then to the several drawings wherein like numerals indicate like parts, and more particularly to FIGS. 3, 4a, and 4b, a first embodiment of sensor 20 is shown wherein resistor 40, having body 46 and leads 48 and 50 at ends 42 and 44, respectively, is partially coated with silicone 22 followed by application of a conductive stratum of carbon particles 26. Conductive stratum 26 is electrically coupled to lead 48 by way of conductive material 32, which also serves as end cap 28. End cap 30, which is conveniently a small tinned brass rivet, is electrically coupled to conductive stratum 26 also by way of conductive material 32, although direct coupling between end cap 30 and stratum 26 may also be employed. End cap 30, and therefore stratum 26, are electrically insulated from lead 50 by way of insulation 34. Both end caps 28 and 30 are intended to provide a suitable means for connecting stratum 26 to other components of the overall invention.

Figure 5:
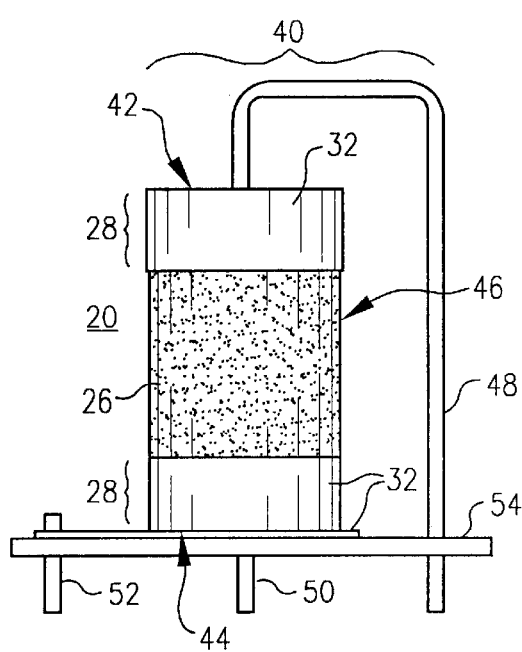
FIG. 5 is an elevation view of an alternative sensor embodiment of the present invention.
Figure 6A:
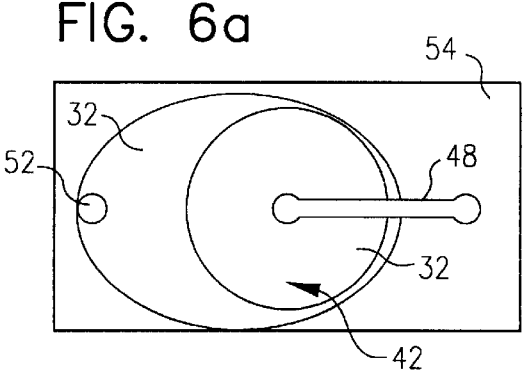
FIG. 6a is a plan view of the sensor in FIG. 5.
Figure 6B:
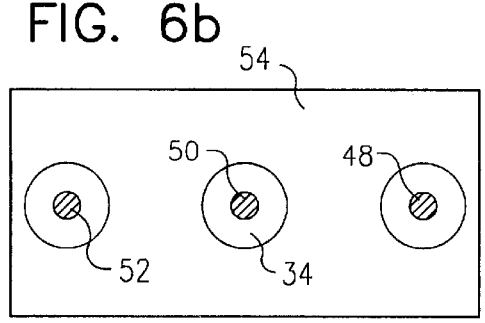
FIG. 6b is a bottom view of the sensor in FIG. 5.

An alternative embodiment of sensor 20 is shown in FIGS. 5, 6a, and 6b. Resistor 40 is shown mounted to board 54. Instead of using end cap 30 as shown in FIGS. 3, 4a, and 4b to provide a suitable means for connecting stratum 26 to other components, conductive material 32 is used at end 44 to provide an electrical pathway between stratum 26 and lead 52, and is therefore similar in respect to end cap 28 at end 42. As with end cap 30, however, there is no electrical connection between stratum 26 and lead 50.

Resistor 40 is preferably a ½ or ¼ watt carbon composition resistor with a resistance value of between 100 and 2,000 ohms. Resistor 40 serves two primary functions: First, it provides a suitable foundation for the application of silicone 22. Second, acts as a resistive heating element or heat source to effectuate an increase the desorption rate of the sensitive surface, namely stratum 26 as will be described in more detail below.

As noted in the previous paragraph, resistor 40 is coated with a layer of silicone 22. Prior to the present invention, the only requirement of the flexible substrate to which the conductive stratum particles were attached or embedded was that it permit physical separation of the particles when the same adsorbed the compounds (adsorbates) for which the sensor was designed to detect and/or measure. Consequently, prior art sensors only specified that "silicone" was an appropriate elastomeric layer. Recent tests have shown that the nature of the "silicone" itself has certain properties that affect the fidelity, reliability, and longevity of the sensor.

In the embodiment described herein, low viscosity (flowable), 100% silicone having no fillers or additives is considered most desirable and produces the highest desorption rates. Most commercially available silicones, such as GE's Silicone II Bathroom Tub & Tile Sealant, contain fillers and anti-fungal or microbial agents. Because most prior art adsorbent sensors are used in damp locations such as boat bilges and underground monitoring wells, such properties were considered desirable in order to limit undesirable biological growth on the sensor. However, in the applications best suited for the present invention, such growth is unlikely given the nature of the immediate environment, i.e., fuel dispenser systems. Consequently, a pure, flowable silicone is preferred because it provides the desired qualities of rapid desorption and long term functionality. In experimental tests, excellent results have been obtained using 100% silicone products from Dow Corning Corporation (Midland, Mich.): 732 clear silicone and Dow 734 RTV self-leveling silicone; and from Permatex: 66 BR and 65AR flowable silicone (self-leveling), with best results being obtained from the self-leveling compositions.

Lastly, it has been found that the sectional thickness of the elastomeric material affects sensor desorption rates. A thinner sectional thickness of material will increase desorption rates in accordance with the teachings of the present invention. In particular, favorable desorption rate increases have been obtained when the sectional thickness of the elastomeric material is less than 10 microns. Moreover and as will be discussed below, exposure of even 100% silicone to organic solvents such as fuel will cause the silicone to expand, thereby jeopardizing the longevity of the sensor.

Applied to the exterior surface of silicone 22 is a stratum of electrically conductive particles 26. Through experimentation, it has been found that smaller particle sizes result in increase desorption rates, up to about 10 microns, in the embodiments built according to the disclosure herein. In this embodiment, carbon particles having a maximum size of 50 microns with a mean size of 10 to 20 microns, and preferably 10 microns, are considered most desirable from a functionality and manufacturing stand point. Carbon particles, i.e., graphite, are considered desirable for the detection of hydrocarbon containing vapor since they are readily available, inexpensive, and have a high affinity for hydrocarbon adsoption, although other conductive particle compositions may be substituted for design considerations. During tests conducted by the inventors, carbon particles obtained from Superior Graphite Company (Chicago, Ill.) having mean diameters of 2.8, 7.1, and 20 were tested and found adequate.

Figure 7:
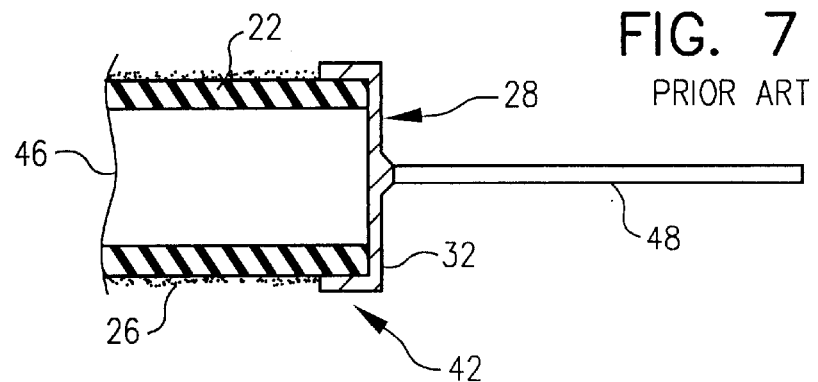
FIG. 7 is a partial cross section of a prior art sensor having a silicone substrate extending to and under an end cap that is electrically coupled to a lead.
Figure 8:
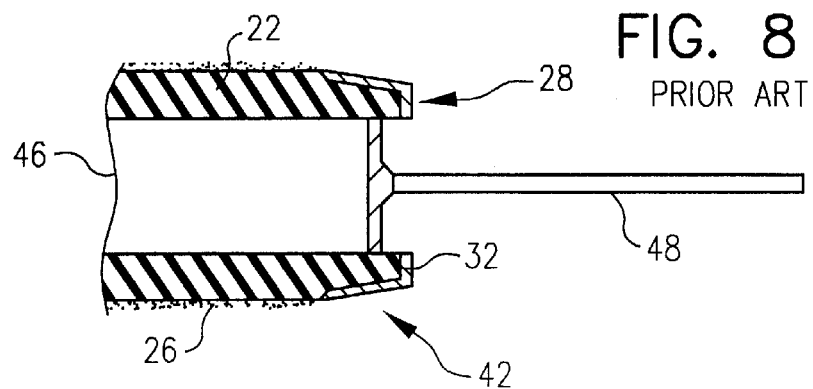
FIG. 8 is a partial cross section of the sensor of FIG. 5 illustrating the deleterious effect of silicone expansion on the end cap after chronic exposure to an organic solvent.

Improvements in long term reliability can be achieved by modifying the nature of silicone 22 application to the exterior of resistor body 46. As shown in relevant portion in FIG. 7, the manufacturing process of a sensor of the prior art will usually result in the application of silicone 22 to either end of body 46. It has been found that long term exposure to solvents such as gasoline vapors or liquid will cause the silicone substrate to radially and longitudinally expand over time. As described earlier and as set forth now in more detail, end cap 28 is preferably formed from an electrically conductive ink sold under part number 102-05F by Creative Materials, Inc. (Tyngsburo, Mass.). This conductive coating does not expand, and will break if a coated substrate does expand. Consequently, end cap 28 will break upon swelling of silicone 22, thereby interrupting the electrical continuity between lead 48 and stratum 26, as is shown in FIG. 8.

Figure 9:
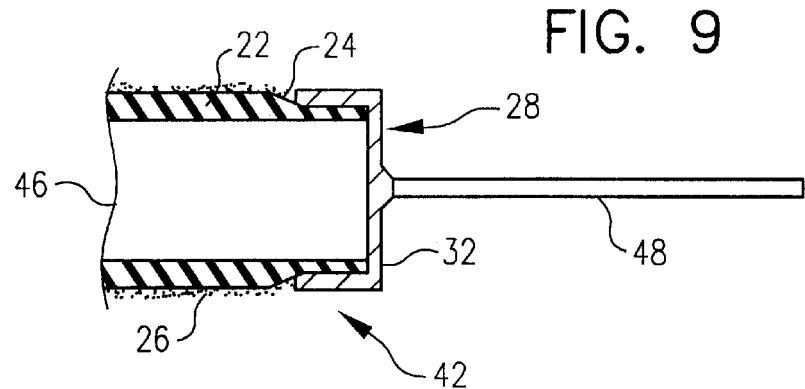
FIG. 9 is a partial cross section of the present invention sensor illustrating a tapered of silicone on the resistor body in relationship to the end cap.
Figure 10:
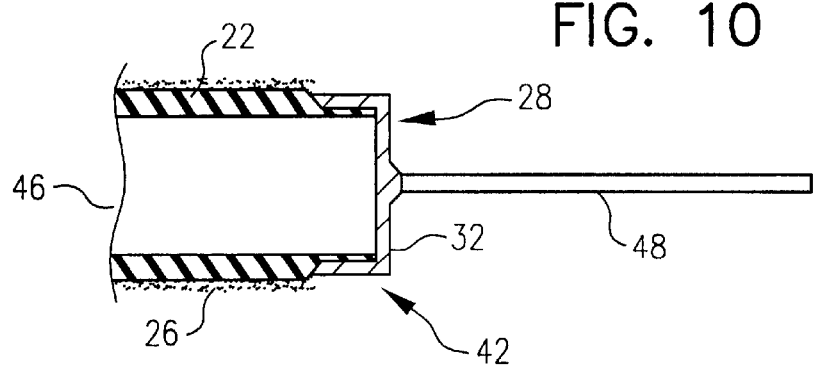
FIG. 10 is a partial cross section of the sensor of FIG. 7 illustrating the effect of a tapered application of silicone on an end cap after chronic exposure to an organic solvent.

To solve this problem, silicone 22 is either not applied or is sparing applied so as to form taper 24, to that portion of resistor body 46, namely end 42, that will receive end cap 28 as shown in FIG. 9. Thus, as illustrated in FIG. 10, when the silicone undergoes eventual expansion, the integrity of end cap 28 is preserved and the continuity between lead 48 and stratum 26 is maintained. Naturally, a rigid end cap such as end cap 30, can be substituted, however, additional steps of establishing continuity between the rigid end cap and the surface would have to be undertaken, likely increasing the manufacturing cost of the sensor.

A significant advance in sensor 20's desorption rate can be achieved by increasing the temperature of conductive stratum 26. It is well known that a substance's vapor pressure can be increased by elevating its temperature. Thus, desorption of stratum 26 can be facilitated by increasing its temperature. This facilitation is accomplished in the preset invention by applying current to leads 48 and 50 of resistor 40. By selecting a resistance value preferably from between 100 and 2,000 ohms, a desirable level of heating is achieved. As will be described below, activation of resistor 40 is only desirable when stratum 26 become overly saturated and adversely affect desorption rates.

This feature of the invention is quite distinct from the prior art use of either resistors or heating components, and represents a simple yet effective method for achieving the desired results. For example, prior sensors chose very high impedance resistors since the resistor's purpose was to provide a surface for elastomeric material adhesion and the resistor leads provided a convenient location for coupling of the sensitive surface. Consequently, these resistors had impedance ratings of 470k ohms to 22 meg ohms since it was considered undesirable to have the resistor consume circuit power. Other prior art sensors attempted to maintain a uniform sensitive surface temperature by employing a complex and power consuming thermo-electric heating and cooling element, and a thermal sensor. Alternatively, this form of temperature regulator could heat the sensitive surface to increase the surface desorption rate. However, because both controlled heating and cooling operations were required, use of a simple resistor having comparatively low impedance values would not have been considered a viable substitute.

Figure 11:
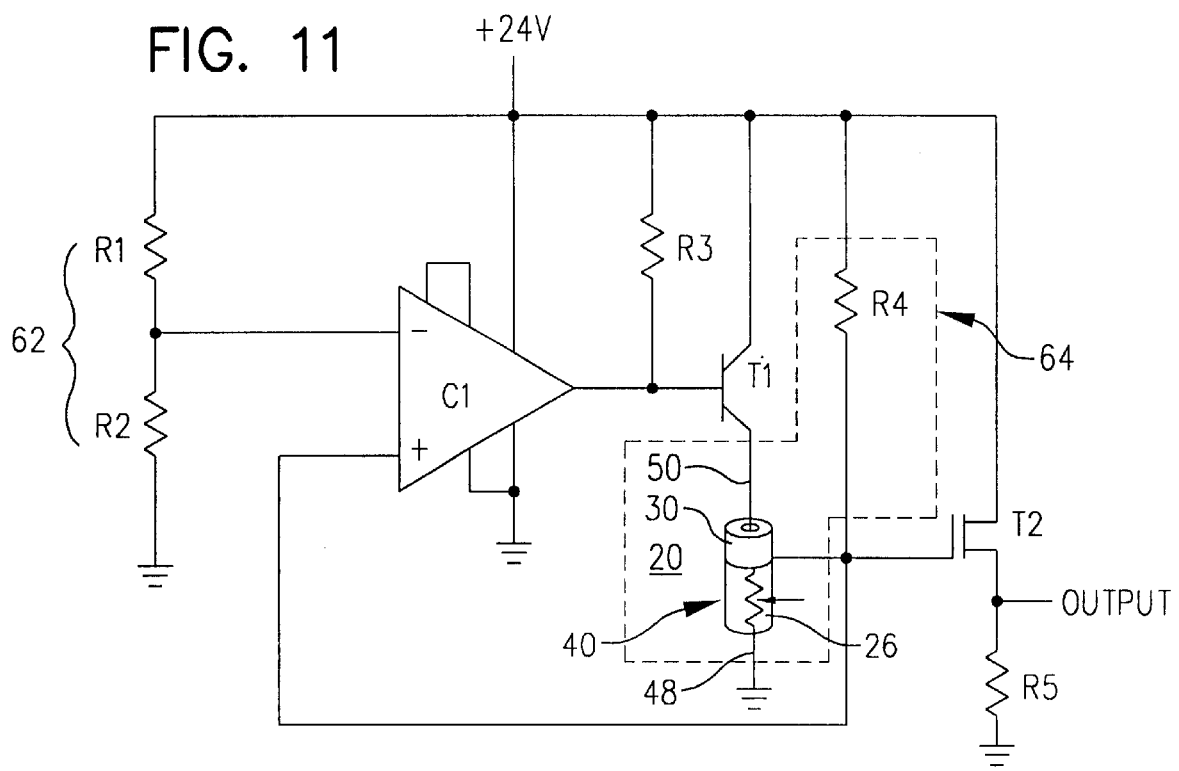
FIG. 11 is a schematic diagram of a control circuit to regulate power distribution to a resistive heating element that is part of the sensor, and to provide amplified output from the sensor to other equipment.

Because continues operation of resistor 40 is not desirable, it is necessary to provide control circuitry for resistor 40. FIG. 11 illustrates in schematic form a preferred control circuitry 60 for use with sensor 20 including resistor 40. In operation, a 24 VDC power supply is coupled to the various components as shown. Voltage comparator C1 (LM311 typical) compares the voltage differential between voltage divider 62 consisting of 1 megohm resistor R1 and 5.1 megohm resistor R2, and voltage divider 64 consisting of 1 megohm resistor R4 and the variable resistance portion of sensor 20. Voltage from comparator C1 will only be supplied to lead 50 when the variable resistance as determined by stratum 26 of sensor 20 exceeds the resistance value of R2. Through experimentation, it has been found that a maximum resistance value is about 5.1 megohms. Because the output of comparator C1 is limited, transistor T1 (2N4401 typical) is employed to supply sufficient current to resistor 40 of sensor 20 to effectuate the desired heating of stratum 26. Field effect transistor T2 (2N7000) is coupled to the power supply and to endcap 30 so that an appropriate signal output can be delivered to auxiliary monitoring and switching equipment. Ten thousand ohm resistors R3 and R5 complete the necessary circuitry.

Figure 12:
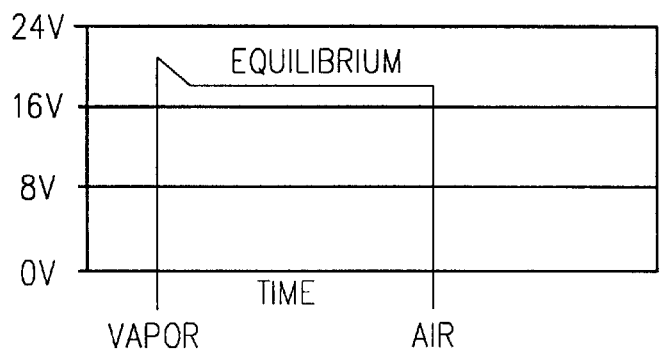
FIG. 12 is a chart of output voltage over time for the control circuit when the sensor is presented with a highly saturated vapor and subsequent presentation of ambient air.

FIG. 12 illustrates the advantageous results of using the described control circuitry when sensor 20 is exposed to a saturated vapor. As shown, the voltage across the sensor at the end caps remains at a maximum regardless of the hydrocarbon partial pressure in the vapor since the maximum resistance of the sensor is limited to about the value of the resistor. Thus, when the sensor is exposed to air containing no such compounds, it is able to respond rapidly through enhanced desorption.

What is claimed:

1. A sensor for use in rapidly sensing the absence of liquids, vapors or gases of interest comprising:
   an electrically resistive element having a first conductive lead and a second conductive lead;
   an elastomeric material in thermal contact with the resistive element; and
   a stratum layer of electrically conductive particles adhered to and at least partially covering the elastomeric material wherein a first portion of the conductive layer is electrically coupled with the first conductive lead; and a third conductive lead is electrically coupled with a second portion of the conductive layer physically apart from the first portion.

2. The sensor of claim 1 wherein the elastomeric material is comprised of a siloxane having the formula $R_2SiO$ wherein R is an alkyl group.

3. The sensor of claim 2 wherein the siloxane is methoxypolydimethylsiloxane.

4. The sensor of claim 1 wherein the elastomeric material is 100% silicone.

5. The sensor of claim 1 wherein the resistive element is a carbon composition resistor.

6. The sensor of claim 5 wherein the resistor has a resistance value of less that 470,000 and more than about 100 ohms.

7. The sensor of claim 1 wherein the electrically conductive particles are composed of the group consisting of platinum, platinum black, aluminum, silver, gold, tantalum, and carbon.

8. The sensor of claim 1 wherein the electrically conductive particles have a maximum size of about 50 microns.

9. The sensor of claim 1 wherein the electrically conductive particles are comprised of carbon particles having a maximum diameter of 50 microns.

10. The sensor of claim 1 wherein the first portion of the conductive layer is electrically coupled with the first conductive lead by a first end cap, and the second portion of the conductive layer is electrically coupled to a second end cap.

11. The sensor of claim 10 wherein the resistive element further has a body portion and the elastomeric material substantially covers the body and tapers towards the first lead.

12. The sensor of claim 1 and a control circuit comprising:
    a first voltage divider and a second voltage divider operatively coupled to a voltage comparator;
    and a power amplifier operatively coupled to an output of the voltage comparator and to the resistive element, wherein the sensor comprises a part of the first voltage divider.

13. The control circuit of claim 12 wherein the first voltage divider comprises the sensor and a first resistor, and wherein the second voltage divider comprises a second and a third resistor.

14. The control circuit of claim 12 further comprising a second power amplifier to increase the sensor output.

15. A sensor to rapidly determine the change in an environment from one containing a relatively high concentration of hydrocarbon containing solvents to one generally without such solvents comprising:
    an electrically resistive element having a body, a first conductive lead, and a second conductive lead wherein the resistance of the element is greater than or equal to 100 ohms and less than or equal to 2,000 ohms;
    an elastomeric material composed essentially of 100% silicone generally surrounding the resistive element body and in thermal contact therewith;
    a stratum layer of carbon particles generally adhered to and at least partially covering the elastomeric material wherein the carbon particles are generally less than or equal to 50 microns, a first portion of the stratum layer is electrically coupled with the first conductive lead; and a third conductive lead is electrically coupled with a second portion of the stratum layer physically apart from the first portion.

16. The sensor of claim 15 further comprising control means for preventing excessive adsorption by the stratum layer of the solvents.

17. A method for rapidly determining the absence of a vapor containing a gas or fluid of interest in an environment comprising the steps of:
    (a) linking a sensor comprising an electrically resistive element having a first conductive lead and a second conductive lead; an elastomeric material in thermal contact with the resistive element; and a stratum layer of electrically conductive particles generally adhered to and at least partially covering the elastomeric material wherein a first portion of the conductive layer is electrically coupled with the first conductive lead; and a third conductive lead is electrically coupled with a second portion of the conductive layer physically apart from the first portion to control means for preventing excessive adsorption by the stratum layer of the gas or fluid of interest;
    (b) exposing the sensor to the environment; and
    (c) monitoring the sensor to determine if an increase in sensor output of a predetermined amount occurs within a predetermined period of time.

18. A method for constructing a sensor assembly comprising the steps of:
    (a) applying a layer of an elastomeric material to the body a resistive element so that the material is in thermal contact with a substantial portion of the resistive element body;
    (b) applying an outer stratum of electrically conductive particles to the elastomeric material so that the stratum is substantially bonded thereto;
    (c) electrically coupling a first portion of the stratum to a first lead of the resistive element; and
    (d) electrically coupling a second portion of the stratum that is physically distant from the first portion to a means for controlling power to the resistive element.

* * * * *